United States Patent
Borghi et al.

[11] Patent Number: 6,056,775
[45] Date of Patent: May 2, 2000

[54] BIFURCATED ENDOVASCULAR STENTS AND METHOD AND APPARATUS FOR THEIR PLACEMENT

[75] Inventors: Enzo Borghi, Budrio, Italy; Anthony Rickards, London, United Kingdom

[73] Assignee: Ave Galway Limited, Galway, Ireland

[21] Appl. No.: 09/000,293

[22] PCT Filed: May 29, 1997

[86] PCT No.: PCT/IB97/00620

§ 371 Date: Jan. 26, 1998

§ 102(e) Date: Jan. 26, 1998

[87] PCT Pub. No.: WO97/45073

PCT Pub. Date: Dec. 4, 1997

[30] Foreign Application Priority Data

May 31, 1996 [IT] Italy ................................. BO96A0294
Apr. 16, 1997 [IT] Italy ................................. BO97A0228

[51] Int. Cl.[7] ...................................................... A61F 2/06
[52] U.S. Cl. ........................................... 623/1.16; 606/195
[58] Field of Search .......................... 623/1, 12; 606/192, 606/194, 195, 108; 600/3; 604/96, 114

[56] References Cited

U.S. PATENT DOCUMENTS

| | | |
|---|---|---|
| 3,657,744 | 4/1972 | Ersek . |
| 4,983,167 | 1/1991 | Sahota . |
| 5,135,536 | 8/1992 | Hillstead . |
| 5,350,395 | 9/1994 | Yock ...................................... 606/194 |
| 5,591,228 | 1/1997 | Edoga ......................................... 623/1 |
| 5,617,878 | 4/1997 | Taheri ...................................... 128/898 |
| 5,626,600 | 5/1997 | Horzewski et al. ..................... 606/194 |
| 5,653,743 | 8/1997 | Martin ........................................ 623/1 |
| 5,709,713 | 1/1998 | Evans et al. ................................ 623/1 |
| 5,755,734 | 5/1998 | Richter et al. ........................... 606/194 |
| 5,814,061 | 9/1998 | Osborne et al. ........................ 606/194 |
| 5,843,164 | 12/1998 | Frantzen et al. ............................ 623/1 |

FOREIGN PATENT DOCUMENTS

| | | |
|---|---|---|
| 0 684 022 | 11/1995 | European Pat. Off. . |
| WO 95/21592 | 8/1995 | WIPO . |
| WO 96/41592 | 12/1996 | WIPO . |
| WO 97/09946 | 3/1997 | WIPO . |

*Primary Examiner*—Bruce Snow
*Attorney, Agent, or Firm*—Sterne, Kessler, Goldstein & Fox P.L.L.C.

[57] ABSTRACT

A bifurcated endovascular stent is formed from a pair of individual tubular component stents that can be placed independently in sequence in the branched region of a body vessel to form the bifurcated stent in situ. The first placed component stent includes a side opening and may be placed to extend both proximally and distally of the bifurcated junction with the side opening facing the entry to the branch vessel. The first component stent then is expanded within the vessel. The second component stent then can be advanced through the first component stent, through the side opening and into the branch vessel where it can be expanded. The portions of the first and second component stents that surround the region of the vessel juncture are constructed to provide enhanced lateral support for the walls of the vessel in the region of the junction. A delivery catheter is provided and includes a guidewire duct adapted to facilitate entry of a guidewire into the branch vessel while the first component stent is being deployed in the other lumen of the vessel.

26 Claims, 8 Drawing Sheets

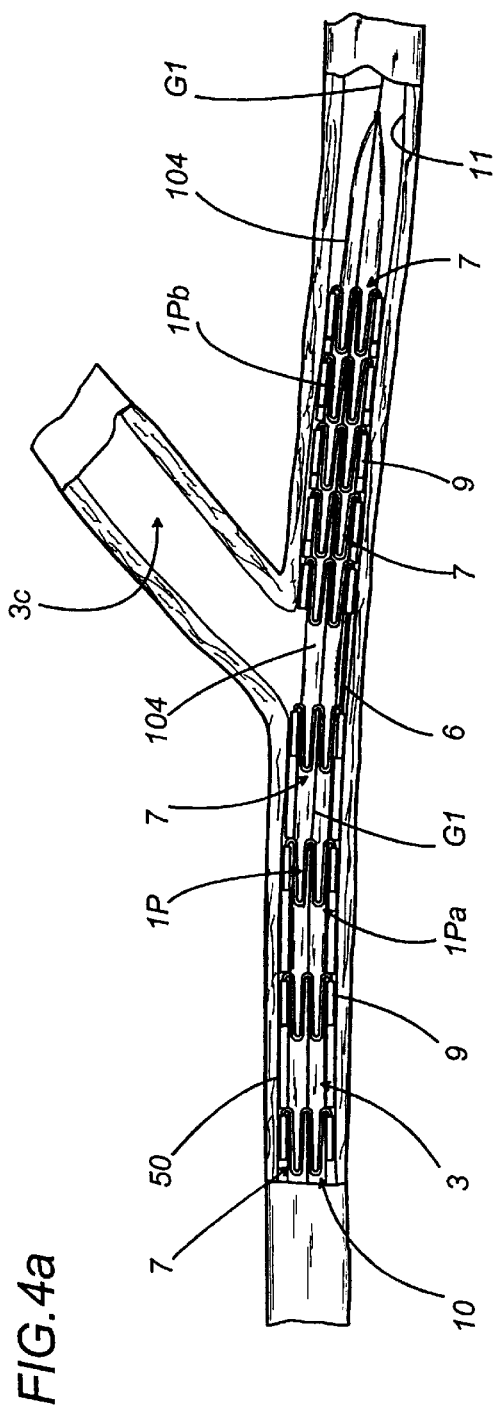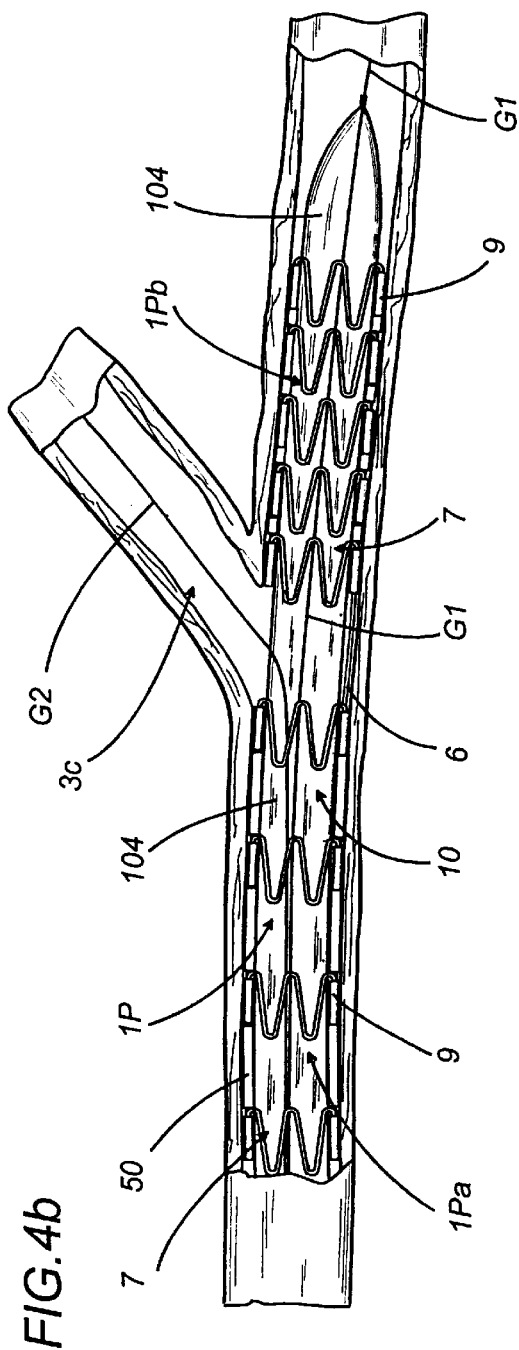
FIG. 4a
FIG. 4b

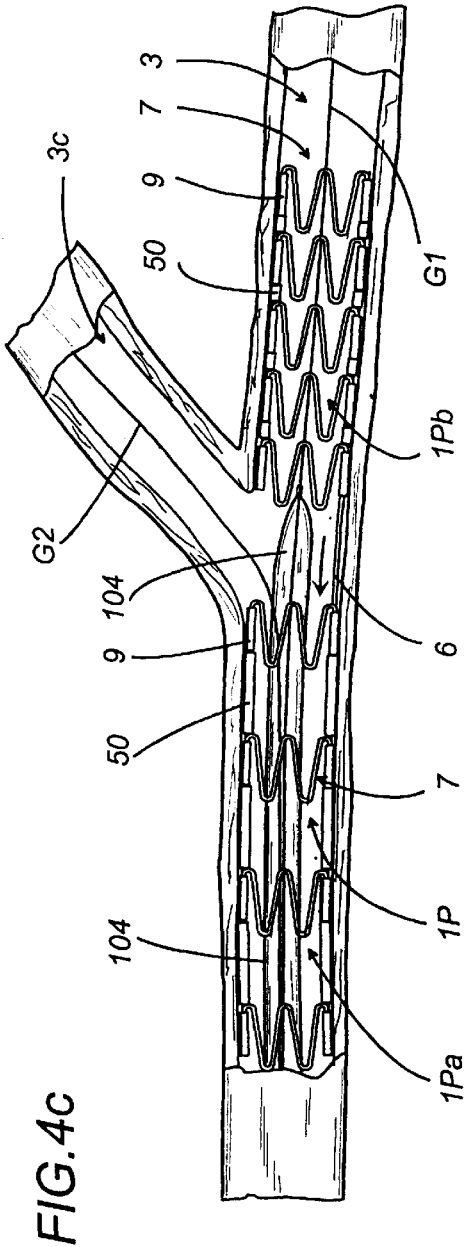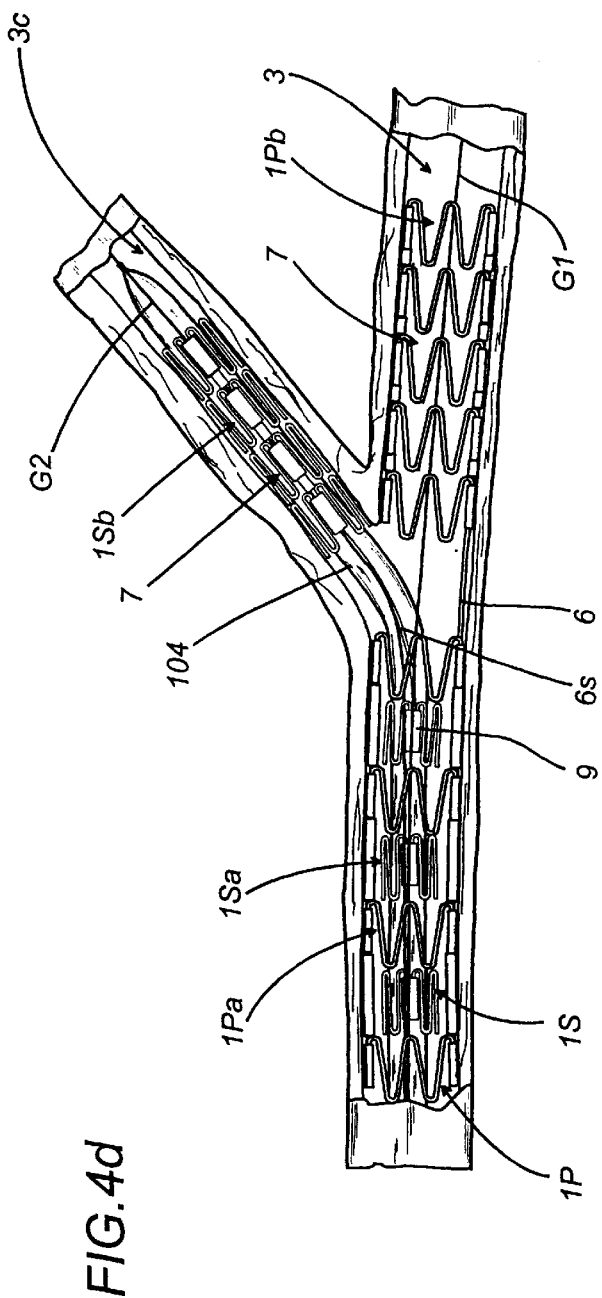
FIG.4c
FIG.4d

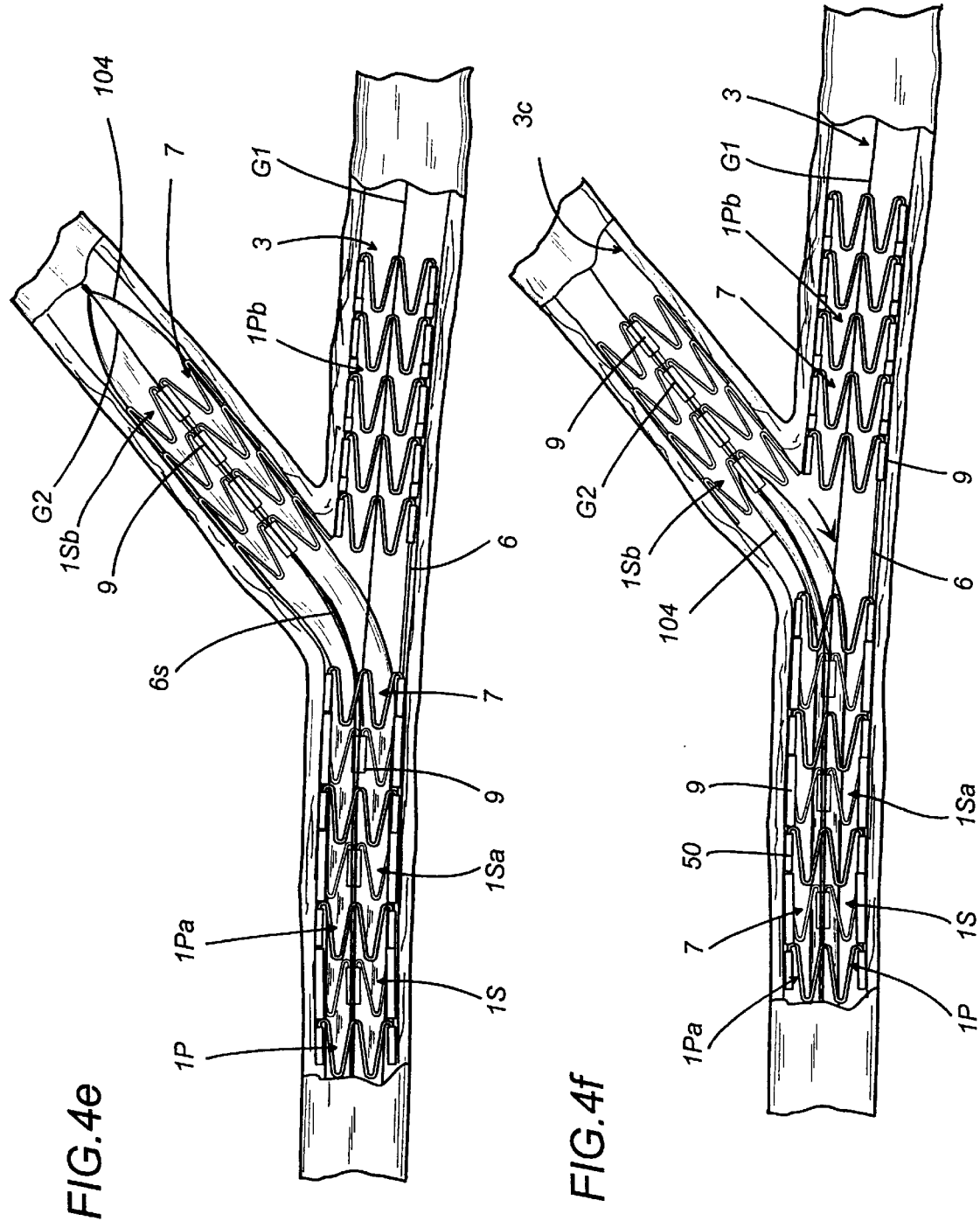

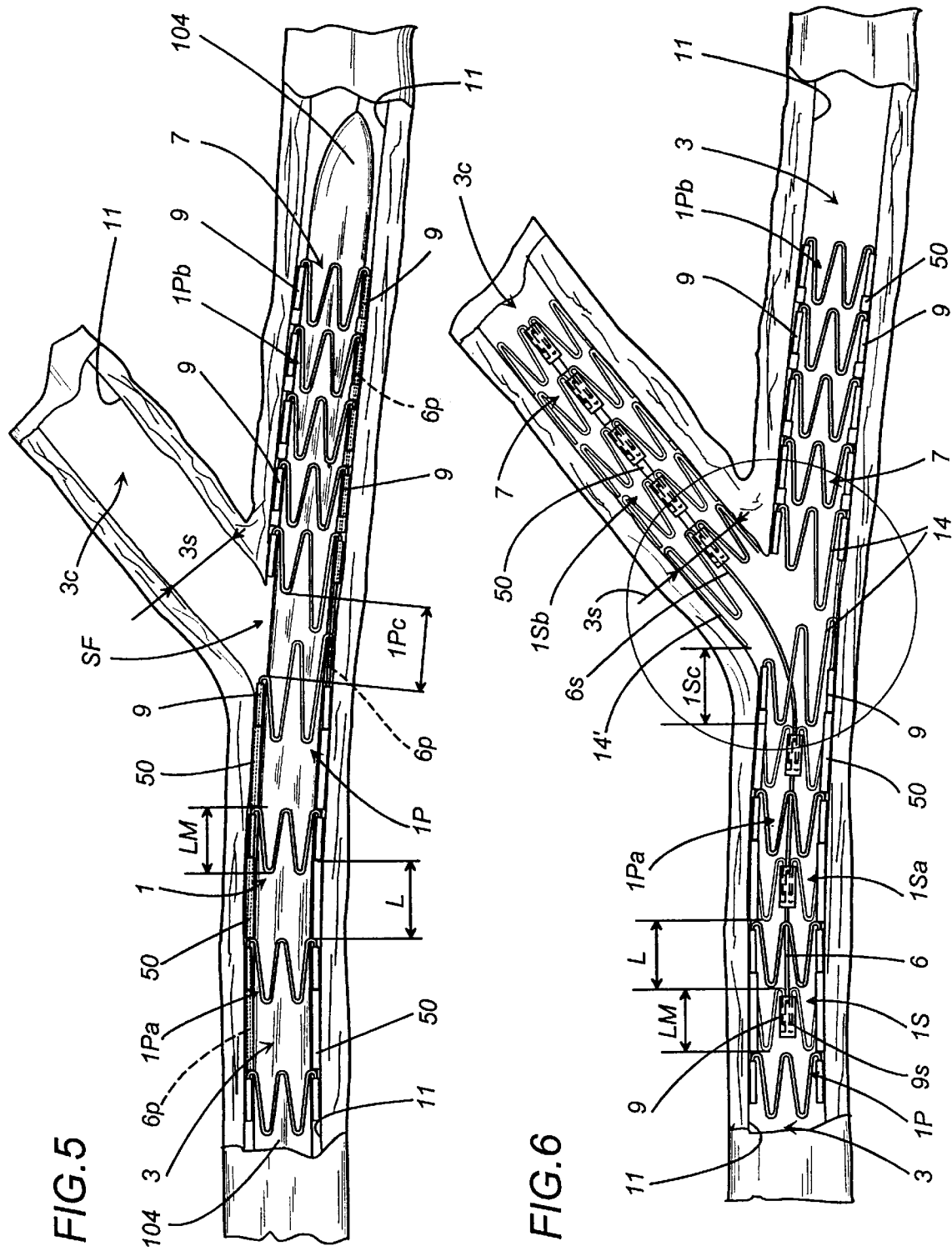

BIFURCATED ENDOVASCULAR STENTS AND METHOD AND APPARATUS FOR THEIR PLACEMENT

TECHNICAL FIELD

The present invention relates to bifurcated endovascular prosthesis implantable in a passage of the human or animal body and to the relative method and apparatus for their placement, prosthesis that are commonly referred to as "stents".

BACKGROUND OF THE INVENTION

A number of medical procedures involve or can be supplemented with the placement of an endoluminal prosthesis, commonly referred to as a stent, that can be implanted in a lumen, such as a blood vessel or other natural pathway of a patient's body. Such stents typically define a generally tubular configuration, and are expandable from a relatively small diameter (low profile) to an enlarged diameter. While in its low profile configuration, the stent is advanced endoluminally, by a delivery device, through the body lumen to the site where the stent is to be placed. The stent then can be expanded to a larger diameter in which it can firmly engage the inner wall of the body lumen. The delivery device then is removed, leaving the implanted stent in place. In that manner, the stent may serve to maintain open a blood vessel or other natural duct, the functioning of which had become impaired as a result of a pathological or traumatic occurrence.

Among the medical procedures in which stents have had increasing use is in connection with percutaneous transluminal angioplasty (PTA), and particularly percutaneous transluminal coronary angioplasty (PTCA). PTA and PTCA involve the insertion and manipulation of a dilating catheter through the patient's arteries to place the dilatation balloon of the catheter within an obstructed portion (stenosis) of a blood vessel. The balloon then is expanded forcibly within the obstruction to dilate that portion of the blood vessel thereby to restore blood flow through the blood vessel. Among the more significant complications that may result from such angioplasty is that in a significant number of cases, the dilated site again becomes obstructed. By placing a stent within the blood vessel at the treated site, the tendency for such restenosis may be reduced.

Stenoses often may develop in the branching region of a patient's blood vessel. Treatment of a stenosis in the branched region may present numerous additional difficulties in the design of devices to dilate stenoses at the branched region.

A number of stents have been proposed and developed in the art, including single stents that define a single luminal pathway as well as bifurcated stents that define a branched pathway and are intended to be placed in a branching region of a blood vessel. The development of bifurcated stents, as compared to single stents, presents numerous difficulties because of the branched arrangement and the difficulty in delivering and placing a bifurcated stent at the branched region of a blood vessel.

In one arrangement, disclosed International Application No. PCT/IB96/00569, filed Jun. 7, 1996, entitled "Bifurcated Endovascular Stent" a bifurcated stent is formed from two, initially independent, component stents. In the preferred embodiment each component stent is formed from wire and has an elongate spine and a plurality of generally tube-defining modules connected to the spine in a longitudinally sequenced array. Each component stent defines a generally tubular configuration. The modules on the two component stents are arranged to enable them to be combined, in situ, to form a bifurcate configuration. Each component stent may be considered to have a proximal set of modules and a distal set of modules. The modules in the proximal set of one component stent are arranged longitudinally to enable them to be interfitted with a complementary module set on the proximal end of the other component stent.

The device is placed at the vessel bifurcation by first inserting one of the component stents to place its proximal module set in the common blood vessel and its distal module set in one of the branches of the blood vessel. The first placed component stent is provided with a side opening between its ends and is placed so that the side opening is positioned at the juncture of the blood vessels to provide access to the branch vessel. The modules in the first component stent then are expanded to secure the first component stent in place. The second component stent then can be advanced into and through the first component stent and transversely through the side opening of the first stent to project the distal module set of the second component stent into the second branch of the blood vessel. With the second component stent so placed, and with its proximal module set aligned to fit in complementary fashion with the proximal module set of the first component stent, the second component stent can be expanded in place.

The present invention is directed to an improved method and apparatus for placing the component stents in a bifurcated configuration in a branched vessel. A further object of the invention is to provide improvements in stent construction by which the stent can provide substantially continuous support for the vessel, including the region of the vessel junction.

DISCLOSURE OF THE INVENTION

In one aspect of the invention, a delivery catheter is provided to deliver and position the first component stent so that the side opening between the proximal and distal module sets is disposed at the juncture of the common and branch blood vessels with the side opening being exposed to the entrance to the branch vessel. The delivery catheter includes a shaft with a stent expansion means, such as a balloon, at its distal end. The first component stent is mountable, in a low profile, on the expansion means. The delivery catheter also includes an elongate tubular guidewire duct that extends along and parallel to the catheter shaft, the distal end of the guidewire duct terminating at about the midportion of and lying exteriorly of the balloon. When the first component stent is mounted on the delivery catheter, it is disposed about the balloon and with the distal region of the guidewire duct being disposed in registry with the side opening of the first component stent.

With the first component stent mounted on the balloon, the catheter can be navigated through the patient's vasculature to place the stent at the vessel bifurcation with its proximal module set disposed in the common blood vessel and the distal module set disposed in one of the branches beyond the junction. The catheter is manipulated into a position, as with the use of a conventional guidewire, so that the side opening is in registry with the lumen of the other branch vessel. When so positioned, a second guidewire is advanced through the guidewire duct and emerges into the branch vessel through a guidewire port at the distal end of the guidewire duct. The expansion means then is operated to expand the first component stent into firm engagement with the blood vessel. The expansion means then can be deactivated and the delivery catheter can be removed from the patient while maintaining the second guidewire in place in the branch vessel. The second component stent, mounted on a balloon delivery device then can be mounted on a delivery device that can be advanced along the second guidewire to guide the delivery device (e.g., a balloon catheter) into the first component stent and laterally through the side opening of the first component stent and into the branch blood vessel. The second component stent is positioned so that its proximal module set is aligned in complementary configuration with the proximal module stent of the first component stent. The second component stent then can be expanded to engage its proximal module set with that of the first component stent and to deploy the distal module set in the branch vessel. The first and second component stents, so placed, cooperate to define a bifurcated stent structure for supporting branched blood vessels.

In another aspect of the invention, the modules of one or both of the component stents that are disposed immediately at the juncture of the blood vessel are formed to provide lateral support for the juncture region of the blood vessels.

Among the objects of the invention is to provide an easily placeable bifurcated endovascular stent.

Another object of the invention is to provide a bifurcated stent that can be placed in the coronary arteries as well as other branched vessels.

Another object of the invention is to provide a bifurcated stent formed from component stents that can be constructed in situ in the branched region of a patient's vasculature.

An additional object of the invention is to provide an endovascular stent that is formed from two generally tubular members, at least one of which has a side opening between its ends to enable part of another stent to be passed partly through the first stent and transversely out of the side opening.

Another object of the invention is to provide a bifurcated stent that can be custom tailored to the vascular anatomy of the patient in whom the device is to be implanted.

A further object of the invention is to provide a bifurcated vascular stent having good radiographic characteristics to facilitate its placement and subsequent visualization of the stent.

A further object of the invention is to provide a delivery catheter adapted to facilitate placement of a first component stent that extends into one branch vessel and a guidewire that extends into the other branch vessel and along which a second component stent can be directed into the other branch vessel.

Another object of the invention is to provide complementary component stents that when placed in the blood vessel provide substantial stenting support in the region of the juncture of branched blood vessels as well as in the branches themselves.

DESCRIPTION OF THE DRAWINGS

The foregoing and other objects and advantages of the invention will be appreciated more fully from the following description thereof, with reference to the accompanying drawings wherein:

FIGS. 4a–4g illustrate, in longitudinal section, the successive steps by which the first and second component stents may be placed to form the bifurcated stent;

FIG. 5 is a longitudinal sectional illustration of a branched blood vessel in which a first component stent has been placed;

FIG. 6 is an illustration similar to FIG. 5 in which the second component has been placed.

DESCRIPTION OF THE ILLUSTRATIVE EMBODIMENTS

Figure 2:
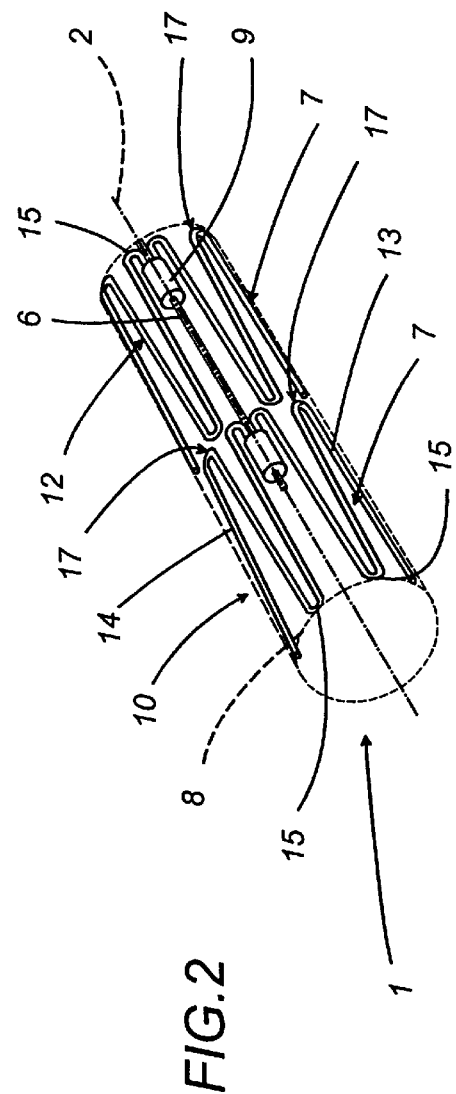
FIG. 2 is a fragmented illustration of a portion of a component stent illustrating a pair of adjacent modules connected to a spine.

FIGS. 2 and 5 illustrate the type of modular endoprosthesis 1 (stent) that may be used in practicing the invention. The endoprosthesis may be considered to define a cage-like tubular arrangement 10 formed from wire-like components and having a central longitudinal axis 2. The stent 1 is constructed from a plurality of individual modules 7 connected to each other along a spine that may be considered to include a longitudinal support wire 6 and connectors 9. The modules 7 are expandable from a contracted, low profile configuration (FIG. 4a), to facilitate placement of the stent in the body lumen, to an enlarged diameter, as suggested in FIG. 4b, in which the modules can be brought into firm engagement with the inner surface of walls 11 of the body lumen 3 to maintain the body lumen open to facilitate blood flow. In the preferred embodiment, the modules are expandable inelastically. The radially expandable, generally tubular, modules 7 are mounted and aligned in longitudinally sequenced array on the support wire 6 by a connector 9 associated with each of the modules 7. The modules, when mounted on the support wire 6, may be considered to define a virtual peripheral surface 12 that, in transverse cross-section, is in the form of a virtual closed curve or loop 8 about the longitudinal axis 2.

Each module 7 is formed from a wire 13 shaped and configured to enable radial expansion of the cylindrical peripheral surface 12. The module may be formed by first forming the wire 13 into a flat serpentine configuration and then wrapping the serpentine wire into its looped configuration. The terminal ends of the serpentine wire are free. The free ends of the wire 13 may be attached to each other and to the support wire 6 by the connector 9. The serpentine arrangement of each of the modules may be considered to include a series of elongate segments 14 alternated with and connected by bends that may be curved (e.g., circular) or may comprise shorter connective segments 15 connected to the elongate segments 14 at cusps 17. The connective bends between the longitudinal segments 14 may lie along and define a locus of the closed loop 8. Preferably, the wire 13 is formed so that the arrangement of bends will be uniformly circumferentially spaced about the virtual closed loop 8 to provide the modules 7 with uniform strength in directions transverse to the support wire 6.

When the modules are in their low profile, unexpanded configuration, the bends 15, 17 that define the connection between adjacent longitudinal segments are such that the elongate segments 14 will lie substantially parallel to each other, defining an angle close to zero degrees. The angle will increase when the module is expanded. The configuration of the connective bends, including the cusps 17 may be varied to vary the angle or to vary their number circumferentially about the closed loop 8 to vary the characteristics of the modules 7, including varying its resistance to compressive radial loads such that the endoprosthesis can further be tailored and made to conform ideally to the specific body lumen 3 in which it is to be implanted.

By way of illustrative example only, a stent may be provided to include modules 7 formed from wire having a diameter of about 0.15 millimeter with elongate segments 14 (not including the connective bends between adjacent segments 14) of a length of about 1.8 millimeters. When the connective bends between adjacent elongate segments 14 are smoothly curved, they may have a radius of about 0.15 millimeter before expansion. A stent having the foregoing dimensions can be expected to be expandable to diameters between about 2.5 to about 4.0 millimeters without excessive expansion, and that such stent exhibits substantial resistance to radial collapse that is well above the maximum radial compressive loads and can be expected to be imposed on the stent by contraction of an artery having a luminal diameter of about 2.5 to about 4.0 millimeters.

In the preferred embodiment the connectors 9 may be constructed to be mounted on the longitudinal support wire 6 as by threading them on the wire 6. The connector 9 preferably may comprise a small tube or ring that defines sufficient internal space to receive and circumscribe the free ends of the wire 13 while also permitting firm connection of the ring to the longitudinal support wire 6. The ring connector 9, free ends of the wire and support wire 6 may be firmly connected by means of a permanent deformation, for example, by crimping, or may be attached to each other by spot welding. When assembled using laser spot welding, it is preferred that the free ends of the wire 13 of the module 7 are first welded to the ring 9 and the ring 9 then is welded to the support wire 6. In some instances, it may be desirable to modify the stent so that one or more of the modules (but not the endmost modules) are not securely attached to the support wire but, instead, are permitted some freedom of sliding movement along the support wire. This may enable making of a final adjustment to the position of the module after the device has been placed in the patient's blood vessel, should that be desired.

The ring connector 9 may be in the form of a relatively short segment of a tube receptive to the support wire 6 and the free ends of the module 7. The internal surface of the ring connector 9 may be contoured to closely match the contour defined by the support wire 6 and free ends of the wire 13 that pass through the connectors 9.

The foregoing construction enables a stent to be specially assembled to conform precisely to the specific anatomy of the patient in whom the stent is to be placed. The modules can be positioned as desired along the support wire 6 and can be secured in that configuration. The support wire 6 may be selected to provide the desired degree of longitudinal flexibility and may be made from wire that is extremely flexible to facilitate positioning of the device in relatively inaccessible body lumen. With the foregoing construction in which the stent has an independent support wire 6, the degree of stiffness or flexibility of the support wire can be selected independently of the wire from which the tubular modules 7 are formed. The support wire 6 may be highly flexible to enable the stent to be carried through narrow, tortuous vessels, such as coronary arteries.

Figure 7:
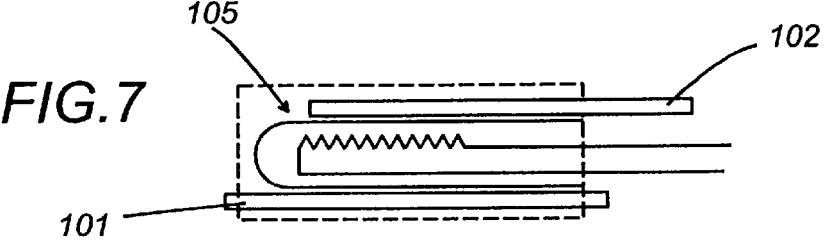
FIG. 7 is a diagrammatic illustration of another stent expansion means utilizing electrical energy for causing expansion of the stent.

It should be understood that although the presently preferred embodiment of the invention incorporates a metal support wire 6 (e.g., stainless steel), the modular construction of the invention enables a fabrication of a stent in which the support wire may be formed from non-metallic materials, such as polymeric materials, for example, nylon or a biologically absorbable material. Other mechanically and biologically suitable classes of materials may be selected, including materials from among those that are biologically absorbable into the tissue of the vessel wall over time. With a bioabsorbable support wire 6, it should be selected to maintain its desirable mechanical characteristics for a sufficient time to enable the modules 7 to become firmly embedded in the vessel wall. The stent modules can be formed from a shape memory material such as a nickel titanium alloy (nitinol) by which the expansion of the module can be effected by a resistance heating element 105 (FIG. 7). Thus, the modular construction of the invention provides a substantially increased range of materials and properties for the individual components, each being selected to provide optimum results. The components of the stent may be coated with a protective material such as carbon or with anticoagulant materials such as heparin. Such variations in materials enables balancing the mechanical strength and the elastic yield of the tubular structure 10 in a manner to enable the stent to be adapted to specific needs of an individual patient.

The ring connectors 9, especially when assembled about the two end segments of the modules 7 and the support wire 6, present a significantly greater mass than that of the wire 13 from which the modules are fashioned. Thus, the region of the spine that includes the ring connectors 9 will present substantially greater radiopacity than that presented by the wire 13 of the associated module. The substantially increased radiopacity of the connected region enhances substantially the radiographic control of the endoprosthesis 1 during implantation. It also enables the prosthesis to be observed radiographically at a later time without requiring use of ultrasound procedures. The configuration of the stent enables the tubular frame 10 to be constructed to have a high mechanical strength while enabling expansion of the device between its low profile and maximum expanded configuration yet in which the wire 13 of the modules 7 will be substantially transparent to X-rays at radiation levels that are typically used in such procedures.

FIGS. 5 and 6 illustrate the placement spacers 50 between pairs of successive connectors 9 before the connectors are secured to the support wire 6. The spacers preferably are cylindrical in shape and have a central hole by which they can be slid, in bead-like fashion, onto and along the longitudinal support wire 6. When a series of connectors 9 and spacers 50 have been placed on the support wire 6, each successive pair of connectors 9 or spacers 50 may embrace one of the other. The length of the spacer(s) may be predetermined to enable precise control over the spacing between two successive modules as well as to reduce the risk of the support wire 6 being twisted or otherwise becoming damaged. In most cases, the spacing of adjacent modules desirably will be such that they can be disposed in close proximity (e.g., with their cusps 17 adjacent each other) to provide substantial continuous support to the vessel wall 11 when the stent has been placed in the patient. Additionally, use of the spacers 50 enables a stent to be assembled with only the two endmost connectors 9 anchored securely to the support wire 6. In such an embodiment, the intermediate components (the connectors 9 and spacers 50) will be retained in position on the support wire and will not separate. Whether all or only the endmost connectors 9 are secured to the longitudinal support wire, the intermediate spacers need not be directly secured to the wire 6 but, instead, can be retained in place by and between their adjacent connectors 9. By way of dimensional example, the cylindrical spacers 50 that may be used with the device having the above-described dimensions may be about 1.10 millimeters in length, 0.30 millimeter in outer diameter and having a wall thickness of about 0.075 millimeter.

The spacers 50, being circular in cross-section, may be arranged to lie substantially flush with the rounded outside face of the adjacent connecting elements. A further advantage in the use of spacers 50 is that together with the ring connectors 9 and the portions of the wire that extend through the rings, the arrangement defines a spine that presents a substantially continuous elongate mass having a radiopacity considerably greater than that of the serpentine wires 13.

All components of the device should be formed from materials that are compatible with each other and will not form microcells that might give rise to electrochemical corrosion of any part of the device after it has been implanted into the blood vessel. The longitudinal support wire 6, wire 13 and connector 9 preferably should have the same chemical composition or compositions that are biologically compatible with each other. Exemplary materials that are preferable in making the endoprosthesis include those from the group of annealed stainless steels, titanium alloys, gold-nickel alloys, nickel-chromium alloys, and titanium-chromium alloys.

The support wire 6 and modules 7 may be treated and formed to vary the mechanical and functional characteristics independently of each other to obtain a desired configuration adapted to treat the anatomy of a specific patient. For example, the wire 13 from which the module is formed may be subjected to an annealing heat treatment to control the malleability of the wire.

FIGS. 5 and 6 illustrate the manner in which a bifurcated stent can be placed in branched blood vessels. In this embodiment, the bifurcated stent is formed from two single (i.e., non-bifurcated) component stents 1P (FIG. 5) and 1S (FIG. 6). The first component stent 1P may be constructed in the manner described above, to include an elongate spine to which a plurality of radially expandable modules 7 are attached. The modules 7 of the stent 1P may be considered to be arranged in sets, including a first (proximal) set 1Pa that may be at the proximal end of the stent 1P and a second (distal) set 1Pb at the other end. The modules 7 in the first set 1Pa are spaced along the spine at predetermined intervals. As described in further detail below, the distance L between the adjacent modules 7 in the first set 1Pa should be sufficient to enable the modules 7 of another stent to be fitted in between the modules 7 in the first set 1Pa. In the preferred embodiment, the predetermined distance is not less than the length LM of one module 7 measured along a direction parallel to the spine. The modules 7 in the second set 1Pb may be arranged in close longitudinal proximity to each other or other spacing that may be appropriate for the particular branch of the vasculature into which it is to be placed. The first component stent 1P also is constructed to have a space 1Pc that defines a side opening SF between the first and second sets 1Pa, 1Pb of module 7. The side opening SF enables a second component stent, in a low profile configuration, to be passed through the first component stent (after expansion of the first component stent) and protrude transversely out of the space 1Pc. By positioning the side opening SF at the juncture of the branched blood vessels, a second component stent can be advanced into the branch artery 3c. In a preferred embodiment, the length of the side opening SF may be approximately that of the diameter 3s of the cross-section of the branch passage 3c. The modules 7 in the first set also may be interconnected by a second longitudinal spine wire 6P, as may be the modules in the second set 1Pb of the first component set 1P. When two spine wires are used, the continuity of the second spine wire 6P (located uppermost as seen in FIG. 5) is interrupted for the length of the side opening SF between the module sets 1Pa and 1Pb. The second component stent preferably is provided only with a single longitudinal spine wire 6s. The stent can be built in situ in the patient by first placing and expanding the first component stent 1P with the side opening SF in registry with one of the branches 3c of the body lumen and then inserting the second component stent 1S through the first component stent 1P and transversely through the side opening SF into the other branch lumen 3c. The proximal ends of the component stents preferably are configured to cooperate with each other to define a common single tube.

The first stent 1P may be delivered to and placed in the artery by a delivery device, described below, having an expansion member that may include a balloon 104. The first stent 1P is mounted on the balloon 104 in a low profile.

The construction of the first component stent 1P includes the arrangement of the spine that may be considered to be defined by the longitudinal support wire 6 and connectors 9. Spacers 50 also may be provided between adjacent pairs of connectors 9. The pattern of connectors 9 or connectors 9 and spacers 50, may be configured to permit distinct radiographic visualization of the space 1Pc at the intermediate portion of the stent to facilitate locating that portion at the desired place in the vascular branched region.

It may be noted that in the illustrative embodiment, the region of the side opening SF in the first component stent 1P is radiographically distinguishable from the other portions of the stent. In the illustrative embodiment that is achieved by omitting spacers or other radiographically observable components along that portion of the spine that extends between the proximal and distal module groups 1Pa, 1Pb. Thus, the spine, in the region 1Pc, is defined only by the support wire 6 which has substantially less mass than the other portions of the spine so that that region can be radiographically distinguished.

The second component stent 1S may be of similar construction to the first component stent 1P, including a first set 1Sa of modules 7 spaced longitudinally to interfit with the spaces between the modules in the first set 1Pa of the first component stent, and a second set of modules 1Sb that may be arranged in close proximity to each other. The first and second module sets 1Sa, 1Sb may be separated by a space 1Sc of a length approximating the diameter of the cross-section 3s of the branch passage 3c. The second component stent may be placed, as described below, by a balloon delivery catheter after at least the first set of modules 1Pa has been expanded into secure engagement with the inner surface of the blood vessel 3. The second component stent 1S is placed longitudinally within the vasculature so that the modules 7 of the proximal set 1Sa of the second component stent is longitudinally aligned with the spaces between the modules 7 on the first set 1Pa of the first component stent 1P. The relative positioning between the sets of modules may be facilitated by the radiopaque portions of the spine, particularly the region of the connectors 9 and, if employed, the spacers 50. With the modules of the first set 1Pa, 1Sa aligned, the modules 7 on the second set may be expanded. The resultant bifurcated stent structure may be configured to define a substantially continuous proximal stent portion within the blood vessel. Similarly, the second sets 1Pb, 1Sb of module 7 are expanded into firm engagement with the portions of the blood vessel branches in which they are placed.

Figure 3:
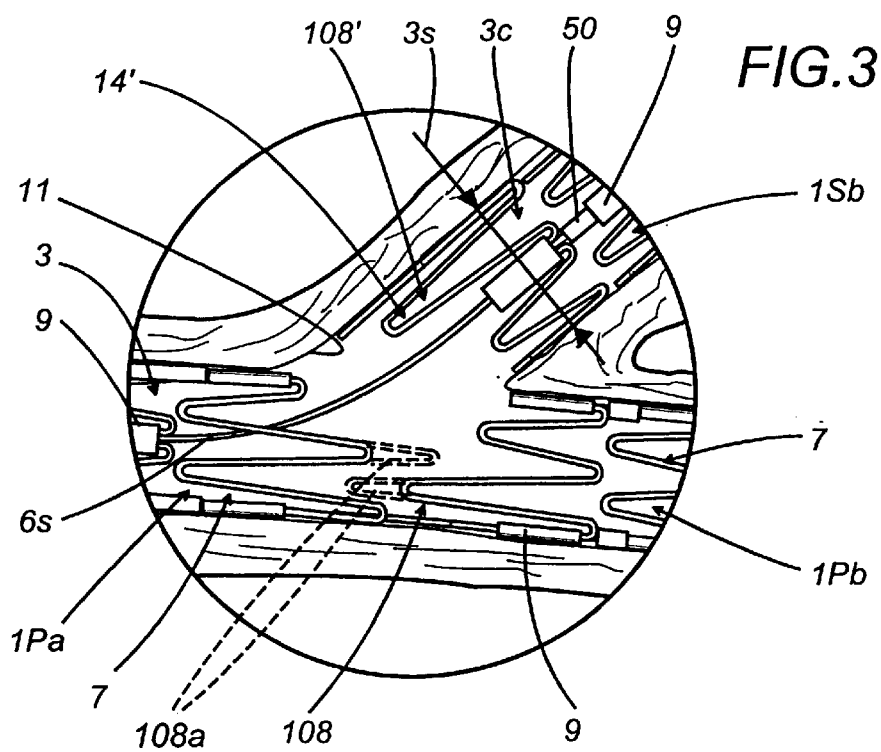
FIG. 3 is an enlarged illustration of the encircled region of FIG. 6 showing the junction region of branched blood vessels and the manner in which the component stents cooperate at that juncture.

In order to enhance the support for the vessel wall 11 at the juncture of the blood vessel branches 3, 3c, either one or both, of the component stents 1P, 1S may be provided with specially constructed modules 7 that, when placed, will border the side opening SF. In such modified modules 7, the longitudinal portions 14, 14' that define the virtual peripheral surface 12 may be formed to have dissimilar lengths so that they may extend into and provide greater support in the region of the juncture, particularly laterally of the region defined by the side opening SF. Thus, the modules 7 at the region of the vessel juncture may be considered to define a virtual cylindrical surface that includes a longitudinally projecting tongue 108 portion of the virtual cylindrical surface thereby to provide additional support for the wall of the juncture but without obstructing the side opening SF. Alternately, one virtual cylinder defined by such a module may be considered to define a virtual surface that is oblique to the longitudinal axis 2 and is defined by the cusps 17 of the module set. Thus, the end modules of each of the modules sets 1Pa, 1Pb in the first component stent 1P may be arranged so that their cusps 15 can be disposed in close proximity to each other. If desired, the tongues of the module 7 may interleave and alternate with each other as suggested in FIG. 3 at 108a. In this manner, the wall 11 of the affected vessels can be better supported with little or no break in continuity along the length of the passage. Similarly, enhanced support may be provided in the region of the juncture associated with the branch passage 3c by providing a tongue 108' on the module 7 of the second component stent 1S disposed at the juncture of the branch passage 3c. The balance between the mechanical strength of the stent 1 and its ability to yield elastically can be optimized further by fashioning the module 7 with the tongue 108 or 108' from a wire 13 having a diameter different from that of the wire used for other of the modules or, alternately, by subjecting the modules to suitable heat treatment before their assembly into the stent.

Figure 1:
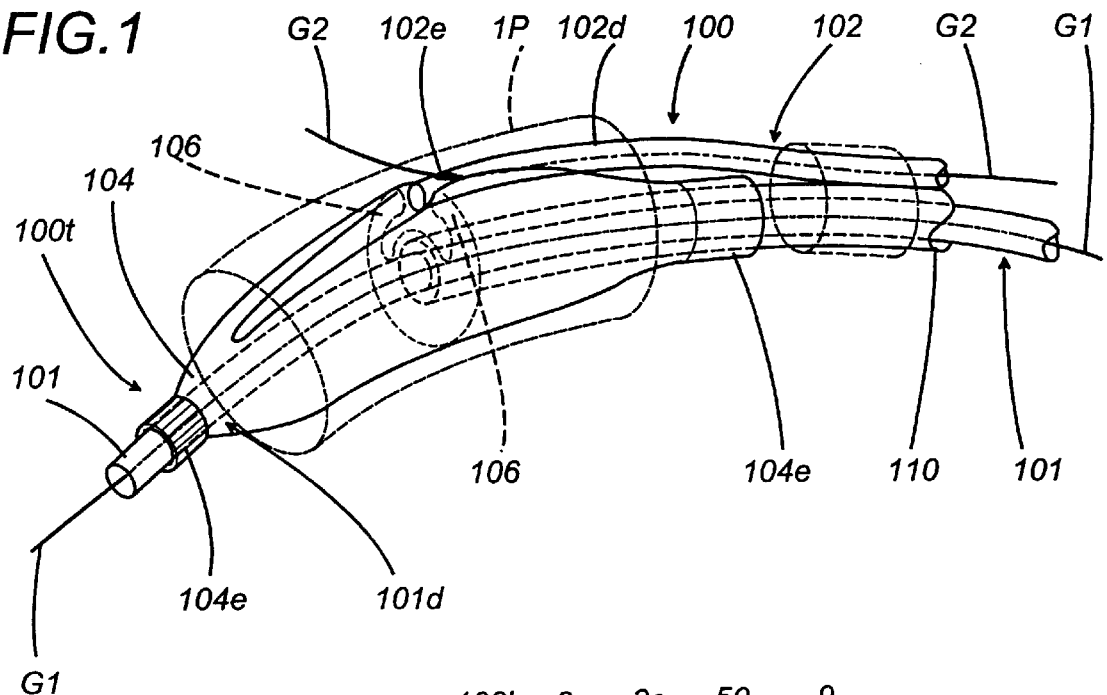
FIG. 1 is an illustration of the distal end of a delivery catheter for placing the first component stent in one of the branch vessels and a guidewire in another branch vessel.

FIG. 1 illustrates a delivery catheter particularly adapted to deliver and place the first component stent of the bifurcated stent in accordance with the invention. It should be understood that although the catheter 100 is illustrated as including an expansion means in the form of an inflatable balloon 104, other expansion means, for example only, an electrical resistance heater 105 (FIG. 7), may be employed. The delivery catheter 100 may have a coaxial shaft including an inner tube 101 disposed within an outer tube 110. The inner tube 101 extends through the balloon to a terminal portion 100t and is open at its distal end. The ends 104e of the balloon are secured to the distal end of the inner and outer tubes 101, 110, as is conventional in coaxial balloon catheters. The annular space defined between the inner tube 101 and the outer tube 110 defines a first lumen through which the balloon can be inflated and deflated. The lumen (defined as second) through the inner tube 101 receives a guidewire G1 to facilitate navigation of the catheter 100.

The delivery catheter also includes an elongate tubular guidewire duct 102 that extends along the catheter shaft and has a distal portion 102d that terminates short of the distal portion 101d of the inner tube 101. The distal end of the guidewire duct 102 is formed to include an exit port 102e oriented to enable a second guidewire G2 to protrude laterally away from the catheter 100. The expansion means, e.g., the balloon 104, is mounted to the catheter so that the guidewire port 102e at the distal portion 102d of the guidewire duct 102 remains exposed. When the stent is loaded onto the catheter, the balloon is folded, as by two folds 106, fashioned to embrace the guidewire duct 102. Alternately, the guidewire duct 102 could be directed through the inflation first lumen 110 and emerge marginally before the point where the balloon is secured as suggested in phantom in FIG. 1. As described below in further detail, when the device is placed in the patient, a second guidewire G2 can be advanced through the guidewire duct 102 and projected laterally through the guidewire port 102e and advanced into the branch passage 3c. It will be appreciated that when the stent is fitted onto the balloon, the distal section 102d of the guidewire duct 102 will be captured between the stent and the balloon. The guidewire port 102e is disposed relative to the stent so that it will be in registry with the side opening SF of the first component stent.

When the expansion means includes an electrical resistance heater 105, preparation of the catheter 100 may comprise the step of locating the heater 105 between the first and second tubes 101, 102 (FIG. 7).

Figure 4G:
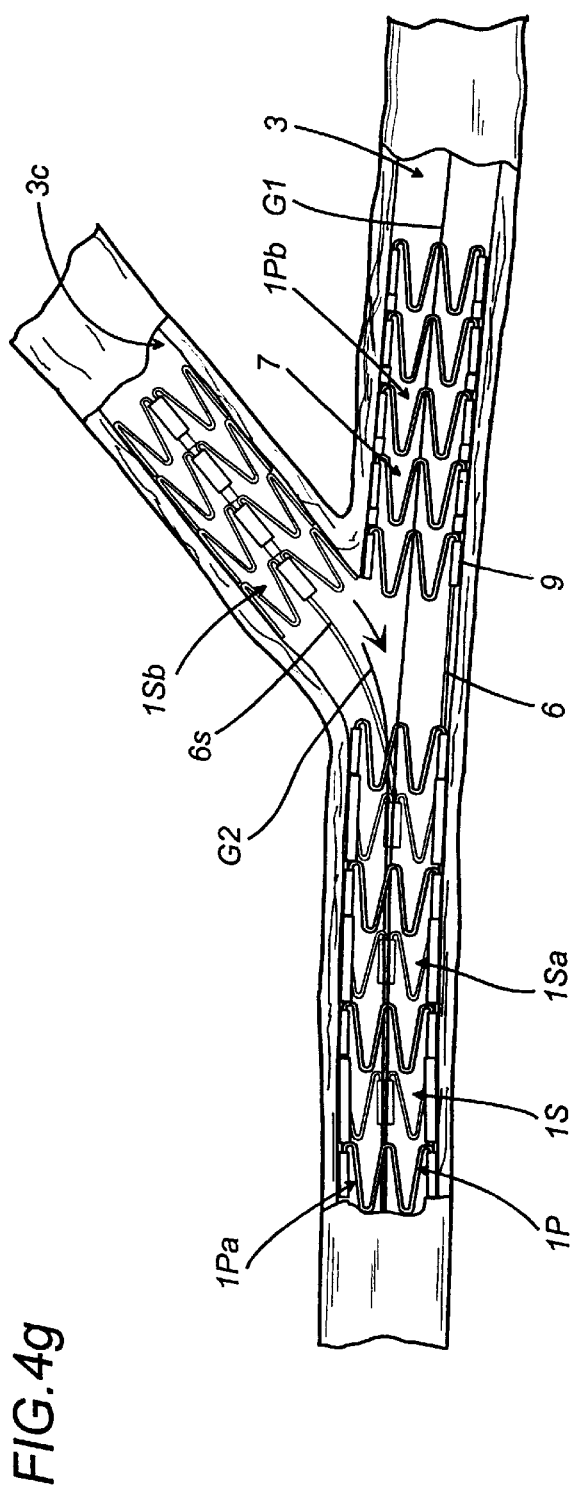

The stent 1 may be fitted on the distal end of the catheter by a loading device such as that described in International Application No. PCT/IB 96/00918, filed Sep. 13, 1996, entitled "Device and Method for Mounting an Endovascular Stent Onto a Balloon Catheter" to which reference is made. The placement and creation of the bifurcated stent, in situ, is illustrated in the sequential drawings of FIGS. 4a–4g. Typically, before the component stents 1P, 1S are placed in the blood vessel, an angioplasty procedure is performed in the blood vessels 3, 3c. The delivery catheter will first be set up with the first guidewire G1 extending through the inner tube 101 of the catheter shaft. The first component stent 1P then is fitted to the catheter 100 about the expansion means 104, 105, with the guidewire port 102e of the guidewire duct 102 in registry with the side opening SF. The catheter 100 then is inserted into the patient's blood vessel and is advanced, along with and with the aid of the guidewire G1 to locate the assembly with the guidewire port 102e disposed at the juncture of the blood vessel branches and facing the branch passage 3c (FIG. 4a). The second guidewire G2 then is inserted into the guidewire duct 102, advancing the guidewire G2 so that its tip emerges from the guidewire port 102e. The guidewire G2 then is advanced into the branch passage 3c (FIG. 4b). The expansion means 104, 105 then is operated to expand the first component stent 1P and stabilize its position in the blood vessel 3 (FIG. 4c). The catheter 100 and guidewire G1 then may be withdrawn from the blood vessel 3 while maintaining the second guidewire G2 in its position within the branch passage 3c (FIG. 4c). The second component stent 1S then is fitted to the same or another catheter in a low profile. That catheter then is advanced along the second guidewire G2 until the second component stent 1S and particularly the second set 1Sb of modules 7 is disposed in the branch passage 3c (FIG. 4d). The expansion means 104, 105 then is operated to expand and stabilize the second component stent 1S within the branch passage 3c and the main passage 3 (FIG. 4e). The second catheter then may be deflated and withdrawn (FIG. 4f). The second guidewire G2 also is withdrawn (FIG. 4g).

It should be appreciated that because of the relative ease by which the connecting elements 9 of the spine can be fluoroscopically monitored, the first and second component stents can be aligned and oriented with respect to each other in the blood vessels. The use of a double spine for the first component stent 1P enhances this ability. A single spine is preferred for the second component stent 1S. The radiopacity of the single spine enables the physician to locate the second component stent 1S to interpose the modules 7 of the first sets 1Pa and 1Sa and with the single longitudinal wire 6 of the second component stent is rotated 90° in relation to the two spines of the first component stent, all parts of the prosthetic structure are readily identifiable (see FIGS. 4d–4g).

Figure 8:
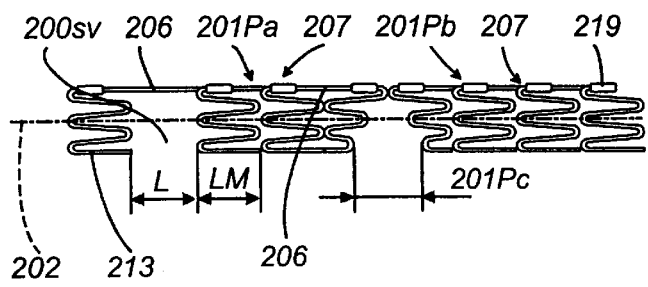
FIG. 8 is a side view of a first component stent in another embodiment of the invention.
Figure 9:
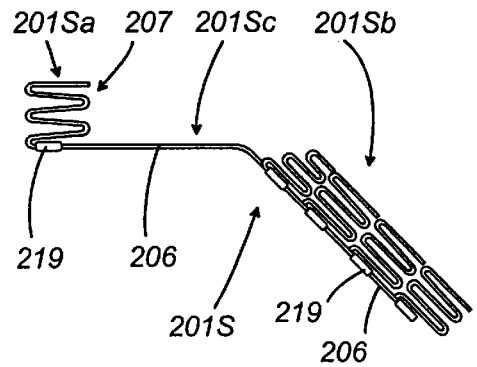
FIG. 9 is a side view of a second component stent adapted for complementary association with the component stent of FIG. 8.
Figure 10:
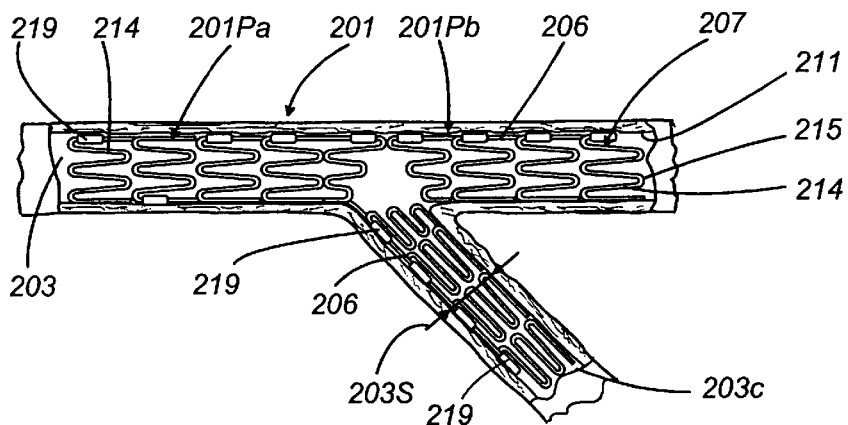
FIG. 10 is a side view of the first and second component stents of FIGS. 8 and 9 assembled to form a bifurcated stent in a bifurcated body vessel.
Figure 11:
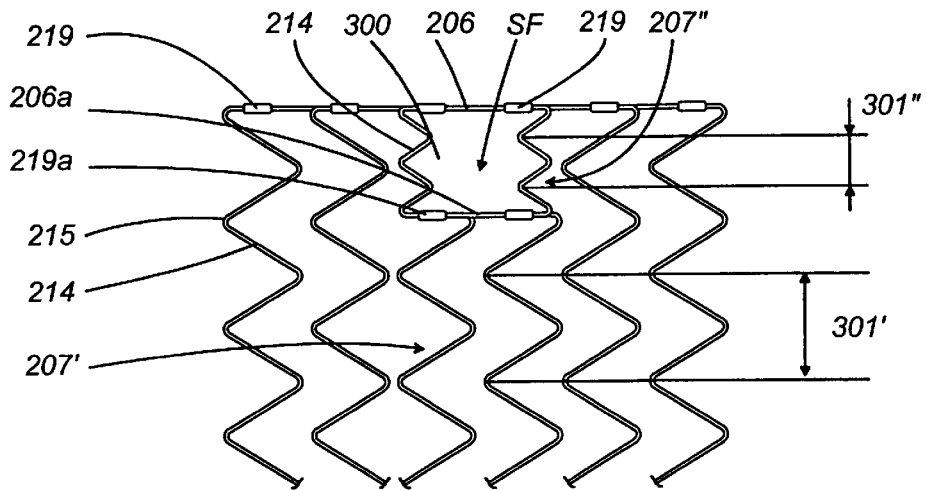
FIG. 11 is an illustration of another embodiment of a component stent with the modules developed in a horizontal plane better to illustrate an arrangement for defining a side opening in the component stent.

FIGS. 8–10 illustrate a variation of the invention. FIGS. 8–10 incorporate reference numerals in a similar pattern to that of the embodiment illustrated in FIGS. 5 and 6 but with the addition of "200" to the reference numeral. Thus, as shown in FIGS. 8–10, the features of the invention and their reference numerals are as follows:

| | |
|---|---|
| space (between two modules) | 200sv |
| stent | 201 |
| first component stent | 201P |
| proximal module set of first component stent | 201Pa |
| distal module set of first component stent | 201Pb |
| space (between proximal and distal module sets) | 201Pc |
| second component stent | 201S |
| proximal module set of second component stent | 201Sa |
| distal module set of second component stent | 201Sb |
| space (between proximal and distal module sets) | 201Sc |
| longitudinal axis | 202 |
| common lumen | 203 |
| branch vessel | 203c |
| branch vessel section | 203s |
| spine wire | 206 |
| module | 207 |
| virtual loop | 208 |
| cage-like tubular arrangement | 210 |
| vessel wall | 211 |
| virtual cylindrical surface | 212 |
| wire | 213 |
| longitudinal segment module | 214 |
| cusp | 215 |
| connector ring | 219 |

The above components function in essentially the same manner as those described above in connection with the embodiments illustrated in FIGS. 5 and 6. In the variation depicted in FIGS. 8–10, however, the proximal module set 201Sa of the second component stent 201S includes only a single module 207 that is adapted to be placed within the single complementary space 200sv in the proximal module set 201Pa of the first component stent 201P. In this embodiment, the L space of 200sv corresponds at least to the width LM of a module 207. The single module proximal set 20Sa is connected to the distal module set 201Sb by a relatively long spine wire 206. It should be noted that although the second component stent is shown in FIG. 9 as being bent in the configuration that it will assume when the two component stents are assembled (FIG. 10), the second component stent will be substantially straight when it is inserted into the previously placed first component stent 201P.

FIGS. 11–14 illustrate further modifications to the stents described above in which the component stents are constructed to still further enhance the support that they provide for the blood vessel in the region of the juncture of the vessels 203, 203c. To that end, the modules 207 located immediately adjacent the side opening 300 (referred to as SF in FIGS. 5 and 6) are assembled from two serpentine wires, one of which (207') has a larger amplitude than the other (207"), that is, one of the serpentine wires has shorter longitudinal portions 214 than the other. The arrangement is apparent from FIG. 11 which illustrates the first component stent with its modules shown as spread out and lying in a flat plane. The serpentine wires that define the modules on each end of the side opening 300 (SF) are constructed from two wires having longitudinal portions 214 that are of different lengths and define a different pitch, as at 301' and 301". The wire that defines the side opening 300 (SF) is formed from the more closely pitched, shorter length serpentine wires. When the first component stent (FIG. 11) is in its cage-like, generally cylindrical configuration, the two modules that lie immediately adjacent the side opening SF may be considered as each being formed from two portions, each portion defining a virtual arcuate element 207', 207". The arcuate wire elements 207', 207" may be connected to each other by connectors 219a. Additionally, a short longitudinal connector wire spine 206a preferably is connected to the ring connectors 219a. The arrangement of the spine wire 206, the short connector wire 206a and the segments 207" cooperate to define a cage-like structure having a high degree of local strength, particularly in the region of the side opening 300 (SF) that will define the entry to the vessel branch 203c when the device is implanted. Additionally, the arrangement of four fluoroscopically visible connector rings 219, 219a arranged in rectangular array about the opening 300 (SF) provides a means by which the position and orientation of the side opening can be verified fluoroscopically.

Figure 12:
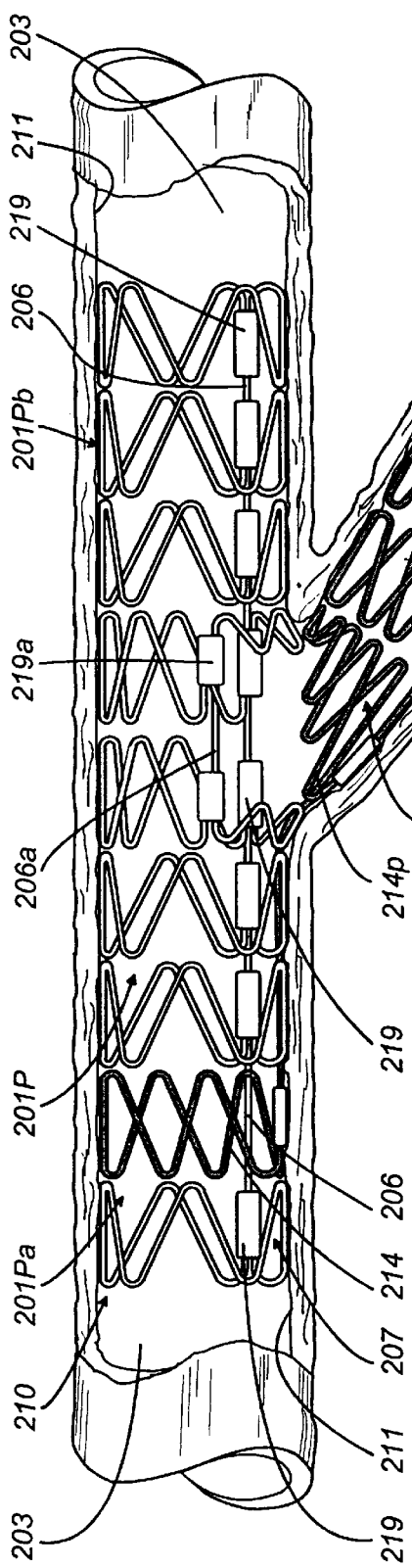
FIG. 12 illustrates a bifurcated endovascular stent formed and in place within a bifurcated blood vessel and incorporating the construction of FIG. 11.
Figure 14:
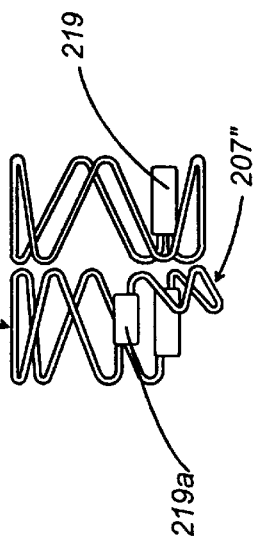
FIG. 14 illustrates a pair of modules of the arrangement as shown in FIG. 12.
Figure 13:
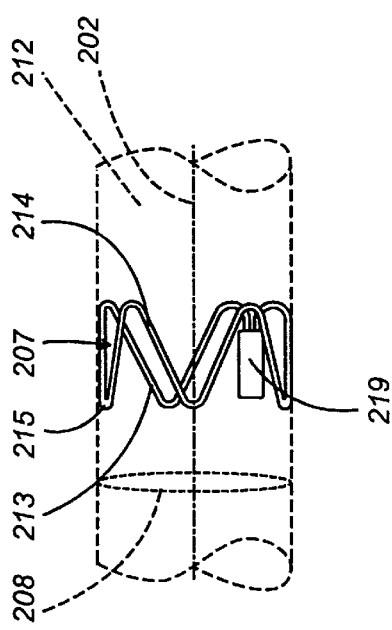
FIG. 13 illustrates further details of a module in the stent shown in FIG. 12.

As shown in FIG. 12, the second component stent 201S includes a module in close proximity to the juncture of the common and branch vessels in which the longitudinal portions 214p of the wire 13 are extended to define a tongue-like configuration as described above in connection with the embodiments of FIGS. 3, 5 and 6. This module associated with the second component stent may be formed in its entirety from a single wire, rather than forming it from two serpentine wires having longitudinal segments 214 of different lengths.

It should be understood that the foregoing description of the invention is intended merely to be illustrative thereof and that other embodiments, modifications and equivalents will be apparent to those skilled in the art without departing from its principles.

What is claimed is:

1. A method for forming a bifurcated stent within a body lumen having a common portion and first and second branches communicating with the common portion at a juncture, comprising the steps of:

providing a first tubular component stent open at each end, having a side opening between its ends, and being expandable radially from a low profile to an expanded configuration;

providing a catheter having an expansion member at a distal end of the catheter and a guidewire duct having a guidewire port located between ends of the expansion member to enable a distal end of a guidewire to extend out of the guidewire port;

mounting a first component stent on the expansion member with the side opening in registry with the guidewire port;

advancing the assembly of the catheter and first component stent to the juncture of the common portion and first and second branches of the body lumen and with the side opening facing an entrance to the second branch, a proximal portion of the first component stent being disposed within the common portion of the body lumen and a distal portion of the first component stent being disposed in the first branch of the body lumen;

operating the expansion member to expand the first component stent within the body lumen into engagement with an interior surface of the body lumen;

advancing a guidewire through the guidewire duct, the guidewire port and into the second branch of the body lumen;

while maintaining the guidewire in its position in the second branch of the body lumen, removing the catheter from the patient;

advancing a second component stent in to the body lumen, guiding the second component stent by the guidewire to place at least a distal portion of the second component stent through the side opening of the first component stent and in the second branch of the body lumen; and expanding the second component stent into engagement with an interior surface of the body lumen.

2. A method as defined in claim 1 wherein the expansion member comprises a balloon, the method further comprising folding a portion of the balloon about the distal portion of the guidewire duct before mounting the first component stent on the balloon, the balloon folding being such as to maintain the guidewire port exposed.

3. A method as defined in claim 2 wherein the step of folding the balloon comprises making at least one on each side of the guidewire duct.

4. A method as defined in claim 1 wherein the expansion member comprises an electrical resistance heater and wherein the step of mounting the first component stent on the catheter comprises locating the heater between a shaft of the catheter and the guidewire duct.

5. A method as defined in claim 1 wherein the catheter includes a shaft that includes a guidewire lumen open at the distal tip of the shaft and where the step of advancing the assembly of the catheter and first component stent comprises preliminarily extending the guidewire from the distal end of the catheter and manipulating the guidewire to provide a path for advancing and guiding the catheter to the intended location of stent placement.

6. A method for placing a component stent of a bifurcate stent assembly comprising the steps of:

mounting the component stent on a delivery device having an expansion member at a distal end of the delivery device, the component stent have a side opening between a distal end and a proximal end of the component stent;

interposing a guidewire duct having a guidewire exit port between the expansion member of the delivery device and the stent, with the guidewire duct having a guidewire exit port in registry with the side opening of the component stent;

advancing the assembled delivery device and component stent through a body lumen to a region of a juncture of a common portion and branches of the body lumen with the side opening and the guidewire exit port facing one of the branches.

7. A component stent for placement at a bifurcated region of a body lumen comprising:

an elongate tube-defining member having a proximal section and a distal section, each of the proximal and distal sections including at least one radially expandable module; and a side opening defined between a distal module of the proximal section and a proximal module of the distal section, wherein a portion of either the distal module of the proximal section or the proximal module of the distal section extends towards and is in close proximity to either the proximal module of the distal section or the distal module of the proximal section to provide substantially continuous support of the body lumen, and wherein the modules are formed from wire arranged in a serpentine pattern including a plurality of elongate segments alternated with shorter connective bends, at least some of the elongate segments on at least one of the distal module of the proximal section or the proximal module of the distal section being longer than other elongate segments of said at least one module.

8. A component stent as defined in claim 7 wherein the elongate segments of said at least one module which are disposed laterally of the side opening are longer than the other elongate segments of said at least one module.

9. A component stent as defined in claim 7 wherein the elongate segments are connected to each other at cusps and where the cusps of the distal module of the proximal portion and the proximal module of the distal portion are disposed in close proximity to each other.

10. A component stent as defined in claim 7 wherein the elongate segments are connected to each other at cusps and where the cusps of one of the distal module of the proximal portion or the proximal module of the distal portion overlaps and extends beyond the cusps of the other of the distal module of the proximal portion or the proximal module of the distal portion.

11. A bifurcated stent comprising:

a first component stent and a second component stent, each of which includes a plurality of modules arranged in a sequence to define a generally tubular configuration; and a side opening defined between a pair of sequentially disposed modules of the first component stent, wherein the second component stent extends through a portion of the first component stent and projects laterally through the side opening, and wherein said pair of modules on the first component stent have side portions disposed laterally of the side opening that extend toward and into proximity with each other, and wherein each module of said pair of modules defining said side opening is formed from wire arranged in a serpentine pattern including elongate segments serially connected to each other by cusps, the elongate segments of said pair of modules being arranged so that some of the cusps of one module of said pair of modules are disposed in close proximity to some of the cusps of the other module of said pair of modules, and wherein some of the cusps of one module of said pair of modules overlap and extend beyond at least one cusp of the other module of said pair of modules.

12. A catheter for delivering a component stent of a bifurcated stent in which the component stent includes a side opening comprising:
   an elongate flexible shaft;
   an expansion member mounted to a distal end of the shaft; and
   an elongate guidewire duct extending longitudinally of the shaft, the guidewire duct having a distal end exposed externally of the expansion member and defining a guidewire exit port at a location disposed longitudinally between the ends of the expansion member, the guidewire exit port being configured to enable a guidewire to emerge from the guidewire duct in a direction that extends at an angle to the longitudinal axis of the catheter.

13. A delivery catheter as defined in claim 12 wherein the catheter shaft is coaxial and includes an inner tube and an outer tube.

14. A delivery catheter as defined in claim 12 wherein the stent is adapted to expand upon the application of heat and where the expansion member comprises means carried by the catheter for applying heat to the component stent.

15. A delivery catheter as defined in claim 12 wherein the expansion member comprises a balloon.

16. A component stent of a bifurcated stent comprising:
   a plurality of loop-like modules connected sequentially to and along a spine to define a generally tubular configuration;
   at least two of the modules being formed from wire arranged in a serpentine pattern to include elongate segments connected to each other at cusps; and
   a pair of sequentially disposed modules defining a side opening;
   wherein at least one of said pair of modules includes elongate segments of different lengths.

17. A component stent as defined in claim 16 wherein said at least one module has a pair of serpentine wires, one of said pair of serpentine wires having elongate segments which are longer than those of the other of said pair of serpentine wires, the serpentine wire with shorter elongate segments being connected to an end of the serpentine wire with longer elongate segments.

18. A component stent as defined in claim 17 wherein the serpentine wire with shorter elongate segments defines the axial ends of the side opening.

19. A component stent as defined in claim 17 wherein the serpentine wire with longer elongate segments defines a portion of the component stent disposed laterally of the side opening.

20. A component stent as defined in claim 18 wherein
   one end of the serpentine wire with shorter elongate segments is connected to the spine, and the other end of the serpentine wire with shorter elongate segments is connected to an end of the serpentine wire with longer elongate segments.

21. A component stent as defined in claim 20 wherein the serpentine wire with the shorter elongate segments is connected to the spine at a connector that has a substantially larger radiographic mass than that of the wire.

22. A component stent as defined in claim 21 wherein the serpentine wire with the shorter elongate segments is connected to the serpentine wire with the longer elongate segments at a connector having substantially greater radiographic mass than the wires.

23. A component stent as defined in claim 26 wherein the connectors that connect the serpentine wire with the shorter elongate segments to the spine and the serpentine wire with the longer elongate segments define a generally rectangular pattern that defines the corners of the side opening.

24. A component as defined in claim 26 further comprising:
   a short connector wire extended between a junction of said serpentine wire with shorter elongate segments and said serpentine wire with longer elongate segments of one of said pair of modules and a junction of said serpentine wire with shorter elongate segments and said serpentine wire with longer elongate segments of the other of said pair of modules.

25. A component stent as defined in claim 17 where the pitch with respect to a longitudinal axis of the stent of the serpentine wire with shorter elongate segments is less than the pitch with respect to a longitudinal axis of the stent of the serpentine wire with longer elongate segments.

26. A component stent as defined in claim 16, wherein each module of said pair of modules includes a pair of serpentine wires, one of said pair of serpentine wires having elongate segments which are longer than those of the other of said pair of serpentine wires, the serpentine wire with shorter elongate segments being connected at one end to the support wire by a connector and at another end to an end of the serpentine wire with longer elongate segments by a connector.

* * * * *